United States Patent
Pencheva et al.

(10) Patent No.: US 11,020,376 B2
(45) Date of Patent: *Jun. 1, 2021

(54) CRYSTALLINE FORM OF LORLATINIB FREE BASE

(71) Applicant: Pfizer Inc., New York, NY (US)

(72) Inventors: Klimentina Dimitrova Pencheva, Sandwich (GB); Melissa Jane Birch, Sandwich (GB); Stephen Mark McAllister, Sandwich (GB); Martin Gregory Rowland, Sandwich (GB); Ian Leonard Smales, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/535,747

(22) Filed: Aug. 8, 2019

(65) Prior Publication Data

US 2019/0365712 A1 Dec. 5, 2019

Related U.S. Application Data

(63) Continuation of application No. 15/743,894, filed as application No. PCT/IB2016/054483 on Jul. 27, 2016, now Pat. No. 10,420,749.

(60) Provisional application No. 62/352,349, filed on Jun. 20, 2016, provisional application No. 62/199,418, filed on Jul. 31, 2015.

(51) Int. Cl.
| | |
|---|---|
| *A61K 31/4162* | (2006.01) |
| *A61P 35/00* | (2006.01) |
| *C07D 498/18* | (2006.01) |
| *G01N 21/65* | (2006.01) |
| *G01N 23/20* | (2018.01) |
| *G01N 24/08* | (2006.01) |

(52) U.S. Cl.
CPC .......... *A61K 31/4162* (2013.01); *A61P 35/00* (2018.01); *C07D 498/18* (2013.01); *C07B 2200/13* (2013.01); *G01N 21/65* (2013.01); *G01N 23/20075* (2013.01); *G01N 24/087* (2013.01)

(58) Field of Classification Search
CPC .......... C07D 498/18; C07B 2200/13
See application file for complete search history.

(56) References Cited

U.S. PATENT DOCUMENTS

| | | |
|---|---|---|
| 8,680,111 B2 | 3/2014 | Bailey et al. |
| 8,916,593 B2 | 12/2014 | Bunnage et al. |
| 9,133,215 B2 | 6/2015 | Bailey et al. |
| 9,637,500 B2 | 5/2017 | Jensen et al. |

FOREIGN PATENT DOCUMENTS

| | | |
|---|---|---|
| WO | 2011/138751 | 11/2011 |
| WO | 2012/121764 | 9/2012 |
| WO | 2013132376 | 9/2013 |
| WO | 2014207606 | 12/2014 |
| WO | 2017175091 | 10/2017 |
| WO | 2019073347 | 4/2019 |

OTHER PUBLICATIONS

Awad et al., "Acquired Resistance to Crizotinib from a Mutation in CD74-ROS1." N Engl J Med 2013; 368:2395-2401.
Birchmeier et al. "Expression and rearrangement of the ROSI gene in human glioblastoma cells." Proc Natl Acad Sci 1987; 84:9270-9274.
Birchmeier et al., "Characterization of an Activated Human ros Gene." Mol. Cell. Bio. 1986; 6(9):3109-3115.
Byrn et al., "Pharmaceutical Solids: A Strategic Approach to Regulatory Considerations." Pharm Res. 1995; 12:945-954.
Caren et al., "High incidence of DNA mutations and gene amplifications of the ALK gene in advanced sporadic neuroblastoma tumors." Biochem. J. 2008; 416:153-159.
Charest et al., "Fusion of FIG to the Receptor Tyrosine Kinase ROS in a Glioblastoma with an Interstitial del(6) (q21q21)." Genes Chromos. Can. 2003; 37(1): 58-71.
Choi et al., "EML4-ALK Mutations in Lung Cancer than Confer Resistance to ALK Inhibitors." N Engl J Med 2010; 363:1734-1739.
Gschwind et al., "The discovery of receptor tyrosine kinases: targets for cancer therapy." Nat. Rev. Cancer 2004; 4, 361-370.
Gu et al. "Survey of Tyrosine Kinase Signaling Reveals ROS Kinase Fusions in Human Cholangiocarcinoma." PLoS ONE 2011; 6(1): e15640.
Hanahan & Weinberg, "The hallmarks of cancer." Cell 2000; 100: 57-70.
International Preliminary Report on Patentability dated Feb. 6, 2018 for International Publication No. WO 2017/021823.
International Search Report completed on Sep. 14, 2016 for International Publication No. WO 2017/021823.
Johnson et al., "Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations" J. Med. Chem. 2014, 57:4720-4744.
Krause & Van Etten, "Tyrosine kinases as targets for cancer therapy." N. Engl. J. Med. 2005; 353: 172-187.

(Continued)

*Primary Examiner* — Kamal A Saeed
(74) *Attorney, Agent, or Firm* — Fariba Shoarinejad

(57) ABSTRACT

This invention relates to acrystalline form of (10R)-7-amino-12-fluoro-2,10,16-trimethyl-5-oxo-10,15,16,17-tetrahydro-2H-8,4-(metheno)pyrazolo[4,3-h] [2,5,11]benzoxadiazacyclo-tetradecine-3-carbonitrile (lorlatinib) free base (Form 7). This invention also relates to pharmaceutical compositions comprising Form 7, and to methods of using Form 7 and such compositions in the treatment of abnormal cell growth, such as cancer, in a mammal.

37 Claims, 8 Drawing Sheets

(56) References Cited

OTHER PUBLICATIONS

Morris et al., "Fusion of a kinase gene, ALK, to a nucleolar protein gene, NPM, in non-Hodgkin's lymphoma." Science 1994; 263:1281-1284.
Nagarajan et al. "The human c-ros gene (ROS) is located at chromosome region 6q166q22." Proc Natl Acad Sci 1986; 83:6568-6572.
Palmer et al., "Anaplastic lymphoma kinase: signaling in development and disease." Biochem. J. 2009; 420:345-361.
Pulford et al., "Anaplastic lymphoma kinase proteins in growth control and cancer." J. Cell Physiol., 2004; 199: 330-58.
Rikova et al., "Global Survey of Phosphotyrosine Signaling Identifies Oncogenic Kinases in Lung Cancer." Cell 2007; 131:1190-1203.
Rimkunas et al., "Analysis of Receptor Tyrosine Kinase ROS1-Positive Tumors in Non-Small Cell Lung Cancer: Identification of FIG-ROS1 Fusion." Clin Cancer Res 2012; 18:4449-4457.
Shaw et al. "Clinical activity of crizotinib in advanced non-small cell lung cancer (NSCLC) harboring ROS1 gene rearrangement." Presented at the Annual Meeting of the American Society of Clinical Oncology, Chicago, Jun. 1-5, 2012.
Soda et al., "Identification of the transforming EML4-ALK fusion gene in non-small cell lung cancer." Nature 2007; 448:561-566.
Soda et al., "A mouse model for EML4-ALK-positive lung cancer." Proc. Natl. Acad. Sci. U.S.A. 2008; 105:19893-19897.
Takeuchi et al., "RET, ROS1 and ALK fusions in lung cancer." Nature Medicine 2012; 18(3):378-381).
Wan et al., "Anaplastic lymphoma kinase activity is essential for the proliferation and survival of anaplastic large cell lymphoma cells." Blood, 2006; 107:1617-1623.
Written Opinion of the International Searching Authority dated Sep. 27, 2016 for International Publication No. WO 2017/021823.
Bavin, M., "Polymorphism in Process Development", Chemistry and Industry, 1989, 527-529.
Beckman, W., "Seeding the Desired Polymorph: Background, Possibilities, Limitations, and Case Studies", Organic Process Research & Development, 2000, 4, 372-383.
Caira, M., "Crystalline Polymorphism of Organic Compounds", Topics in Current Chemistry, vol. 198, 164-208 © Springer Verlag Berlin Heidelberg 1998.
Day, G., "Investigating the latent polymorphism of maleic acid", Chem. Commun., 2006, 54-56.
Pirttimaki, J., "Effects of grinding and compression on crystal structure of anhydrous caffeine", International Journal of Pharmaceutics, 95 (1993) 93-99.
Suryanarayanan, R., "Determination of the Relative Amounts of a-carbamazepine and B-carbamazepine in a Mixture by Powder X-Ray Diffractometry", Powder Diffraction, vol. 5, No. 3, Sep. 1990.
Yokoyama, T., et. al., "Kinetic Study on the Isothermal Transition of Benoxaprofen Polymorphs in the Solid State at High Temperature", Chem. Pharm. Bull., 34(2), 917-921, 1986.
Pre-Grant Opposition filed by "Indian Pharmaceutical Alliance" dated Sep. 14, 2019, not yet notified by the Indian Patent office, but found in a review of the Indian Patent Office Website and communicated to Pfizer on Jan. 22, 2021.

CRYSTALLINE FORM OF LORLATINIB FREE BASE

CROSS-REFERENCE TO RELATED APPLICATIONS

This Application is a Continuation of U.S. patent application Ser. No. 15/743,894, filed Jan. 11, 2018, which is the national stage filing under 35 U.S.C. 371 of Patent Cooperation Treaty Patent Application No. PCT/IB2016/054483, filed Jul. 27, 2016, which claims the benefit of priority from U.S. Provisional Application No. 62/352,349 filed Jun. 20, 2016 and U.S. Provisional Application No. 62/199,418 filed Jul. 31, 2015, the contents of each of which are hereby incorporated by reference in their entireties.

FIELD OF THE INVENTION

This invention relates to a new crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiaza-cyclotetradecine-3-carbonitrile (lorlatinib) free base (Form 7), to pharmaceutical compositions comprising Form 7, and to methods of using Form 7 and such compositions in the treatment of abnormal cell growth in mammals.

BACKGROUND OF THE INVENTION

The compound (10R)-7-amino-12-fluoro-2,10,16-trimethyl-15-oxo-10,15,16,17-tetrahydro-2H-8,4-(metheno)pyrazolo[4,3-h][2,5,11] benzoxadiazacyclotetradecine-3-carbonitrile (PF-06463922), represented by the formula (I):

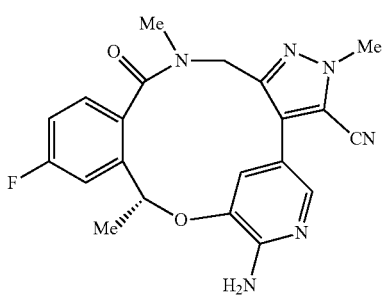

(I)

has been assigned the International Nonproprietary Name (INN) lorlatinib, as described in *WHO Drug Information*, Vol. 29, No. 4, page 541 (2015). Lorlatinib is a potent, macrocyclic inhibitor of both wild type and resistance mutant forms of anaplastic lymphoma kinase (ALK) and c-ros oncogene 1 (ROS1) receptor tyrosine kinase.

Preparation of the free base of lorlatinib as an amorphous solid is disclosed in International Patent Publication No. WO 2013/132376 and in U.S. Pat. No. 8,680,111. Solvated forms of lorlatinib free base are disclosed in International Patent Publication No. WO 2014/207606. The contents of each of the foregoing documents are incorporated herein by reference in their entirety.

Human cancers comprise a diverse array of diseases that collectively are one of the leading causes of death in developed countries throughout the world (American Cancer Society, Cancer Facts and Figures 2005. Atlanta: American Cancer Society; 2005). The progression of cancers is caused by a complex series of multiple genetic and molecular events including gene mutations, chromosomal translocations, and karyotypic abnormalities (Hanahan & Weinberg, The hallmarks of cancer. Cell 2000; 100: 57-70). Although the underlying genetic causes of cancer are both diverse and complex, each cancer type has been observed to exhibit common traits and acquired capabilities that facilitate its progression. These acquired capabilities include dysregulated cell growth, sustained ability to recruit blood vessels (i.e., angiogenesis), and ability of tumor cells to spread locally as well as metastasize to secondary organ sites (Hanahan & Weinberg 2000). Therefore, the ability to identify novel therapeutic agents that inhibit molecular targets that are altered during cancer progression or target multiple processes that are common to cancer progression in a variety of tumors presents a significant unmet need.

Receptor tyrosine kinases (RTKs) play fundamental roles in cellular processes, including cell proliferation, migration, metabolism, differentiation, and survival. RTK activity is tightly controlled in normal cells. The constitutively enhanced RTK activities from point mutation, amplification, and rearrangement of the corresponding genes have been implicated in the development and progression of many types of cancer. (Gschwind et al., The discovery of receptor tyrosine kinases: targets for cancer therapy. Nat. Rev. Cancer 2004; 4, 361-370; Krause & Van Etten, Tyrosine kinases as targets for cancer therapy. N. Engl. J. Med. 2005; 353: 172-187.)

Anaplastic lymphoma kinase (ALK) is a receptor tyrosine kinase, grouped together with leukocyte tyrosine kinase (LTK) to a subfamily within the insulin receptor (IR) superfamily. ALK was first discovered as a fusion protein with nucleophosmin (NPM) in anaplastic large cell lymphoma (ALCL) cell lines in 1994. (Morris et al., Fusion of a kinase gene, ALK, to a nucleolar protein gene, NPM, in non-Hodgkin's lymphoma. Science 1994; 263:1281-1284.) NPM-ALK, which results from a chromosomal translocation, is implicated in the pathogenesis of human anaplastic large cell lymphoma (ALCL) (Pulford et al., Anaplastic lymphoma kinase proteins in growth control and cancer. J. Cell Physiol., 2004; 199: 330-58). The roles of aberrant expression of constitutively active ALK chimeric proteins in the pathogenesis of ALCL have been defined (Wan et. al., Anaplastic lymphoma kinase activity is essential for the proliferation and survival of anaplastic large cell lymphoma cells. Blood, 2006; 107:1617-1623). Other chromosomal rearrangements resulting in ALK fusions have been subsequently detected in ALCL (50-60%), inflammatory myofibroblastic tumors (27%), and non-small-cell lung cancer (NSCLC) (2-7%). (Palmer et al., Anaplastic lymphoma kinase: signaling in development and disease. Biochem. J. 2009; 420:345-361.)

The EML4-ALK fusion gene, comprising portions of the echinoderm microtubule associated protein-like 4 (EML4) gene and the ALK gene, was first discovered in NSCLC archived clinical specimens and cell lines. (Soda et al., Identification of the transforming EML4-ALK fusion gene in non-small cell lung cancer. Nature 2007; 448:561-566; Rikova et al., Cell 2007; 131:1190-1203.) EML4-ALK fusion variants were demonstrated to transform NIH-3T3 fibroblasts and cause lung adenocarcinoma when expressed in transgenic mice, confirming the potent oncogenic activity of the EML4-ALK fusion kinase. (Soda et al., A mouse model for EML4-ALK-positive lung cancer. Proc. Natl. Acad. Sci. U.S.A. 2008; 105:19893-19897.) Oncogenic mutations of ALK in both familial and sporadic cases of neuroblastoma have also been reported. (Caren et al., High incidence of DNA mutations and gene amplifications of the ALK gene in advanced sporadic neuroblastoma tumors. Biochem. J. 2008; 416:153-159.)

ROS1 is a proto-oncogene receptor tyrosine kinase that belongs to the insulin receptor subfamily, and is involved in cell proliferation and differentiation processes. (Nagarajan et al. Proc Natl Acad Sci 1986; 83:6568-6572). ROS1 is expressed, in humans, in epithelial cells of a variety of different tissues. Defects in ROS1 expression and/or activation have been found in glioblastoma, as well as tumors of the central nervous system (Charest et al., Genes Chromos. Can. 2003; 37(1): 58-71). Genetic alterations involving ROS1 that result in aberrant fusion proteins of ROS1 kinase have been described, including the FIG-ROS1 deletion translocation in glioblastoma (Charest et al. (2003); Birchmeier et al. Proc Natl Acad Sci 1987; 84:9270-9274; and NSCLC (Rimkunas et al., Analysis of Receptor Tyrosine Kinase ROS1-Positive Tumors in Non-Small Cell Lung Cancer: Identification of FIG-ROS1 Fusion, Clin Cancer Res 2012; 18:4449-4457), the SLC34A2-ROS1 translocation in NSCLC (Rikova et al. Cell 2007; 131:1190-1203), the CD74-ROS1 translocation in NSCLC (Rikova et al. (2007)) and cholangiocarcinoma (Gu et al. PLoS ONE 2011; 6(1): e15640), and a truncated, active form of ROS1 known to drive tumor growth in mice (Birchmeier et al. Mol. Cell. Bio. 1986; 6(9):3109-3115). Additional fusions, including TPM3-ROS1, SDC4-ROS1, EZR-ROS1 and LRIG3-ROS1, have been reported in lung cancer patient tumor samples (Takeuchi et al., RET, ROS1 and ALK fusions in lung cancer, Nature Medicine 2012; 18(3):378-381).

The ALK/ROS1/c-MET inhibitor crizotinib was approved in 2011 for the treatment of patients with locally advanced or metastatic NSCLC that is ALK-positive as detected by an FDA-approved test. Crizotinib has also shown efficacy in treatment of NSCLC with ROS1 translocations. (Shaw et al. Clinical activity of crizotinib in advanced non-small cell lung cancer (NSCLC) harboring ROS1 gene rearrangement. Presented at the Annual Meeting of the American Society of Clinical Oncology, Chicago, Jun. 1-5, 2012.) As observed clinically for other tyrosine kinase inhibitors, mutations in ALK and ROS1 that confer resistance to ALK inhibitors have been described (Choi et al., EML4-ALK Mutations in Lung Cancer than Confer Resistance to ALK Inhibitors, N Engl J Med 2010; 363:1734-1739; Awad et al., Acquired Resistance to Crizotinib from a Mutation in CD74-ROS1, N Engl J Med 2013; 368:2395-2401).

Thus, ALK and ROS1 are attractive molecular targets for cancer therapeutic intervention. There remains a need to identify compounds having novel activity profiles against wild-type and mutant forms of ALK and ROS1.

The present invention provides a novel crystalline form of lorlatinib free base (Form 7) having desirable properties, such as high crystallinity, high purity, low hygroscopicity, and favorable dissolution and mechanical properties. In particular, Form 7 provides improved physical stability in the drug product formulation relative to the acetic acid solvate disclosed in International Patent Publication No. WO 2014/207606. Such solvated forms may present challenges for drug development, in particular with respect to physical stability. Consequently, there remains a need to identify novel forms having desirable physicochemical properties.

SUMMARY OF THE INVENTION

In one aspect, the invention provides a novel crystalline form of lorlatinib free base (Form 7). Form 7 of lorlatinib free base is characterized by one or more of the following methods: (1) powder X-ray diffraction (PXRD) (2θ); (2) Raman spectroscopy ($cm^{-1}$); (3) $^{13}C$ solid state NMR spectroscopy (ppm); or (4) $^{19}F$ solid state NMR spectroscopy (ppm).

In a first aspect, the invention provides lorlatinib free base (Form 7), which is characterized by having:

(1) a powder X-ray diffraction (PXRD) pattern (2θ) comprising: (a) one, two, three, four, five, or more than five peaks selected from the group consisting of the peaks in Table 1 in °2θ±0.2 °2θ; (b) one, two, three, four, five, or more than five peaks selected from the group consisting of the characteristic peaks in Table 1 in °2θ±0.2 °2θ; or (c) peaks at 2θ values essentially the same as shown in FIG. 1; or (2) a Raman spectrum comprising: (a) one, two, three, four, five, or more than five wavenumber ($cm^{-1}$) values selected from the group consisting of the values in Table 2 in $cm^{-1}$±2 $cm^{-1}$; (b) one, two, three, four, five, or more than five wavenumber ($cm^{-1}$) values selected from the group consisting of the characteristic values in Table 2 in $cm^{-1}$±2 $cm^{-1}$; or (c) wavenumber ($cm^{-1}$) values essentially the same as shown in FIG. 2; or (3) a $^{13}C$ solid state NMR spectrum (ppm) comprising: (a) one, two, three, four, five, or more than five resonance (ppm) values selected from the group consisting of the values in Table 3 in ppm±0.2 ppm; (b) one, two, three, four, five, or more than five resonance (ppm) values selected from the group consisting of the characteristic values in Table 3 in ppm±0.2 ppm; or (c) resonance (ppm) values essentially the same as shown in FIG. 3; or (4) a $^{19}F$ solid state NMR spectrum (ppm) comprising: (a) one or two resonance (ppm) values selected from the group consisting of the values in Table 4 in ppm±0.2 ppm; or (b) resonance (ppm) values essentially the same as shown in FIG. 4;

or a combination of any two, three or four of the foregoing embodiments (1)(a)-(c), (2)(a)-(c), (3)(a)-(c), or (4)(a)-(b), provided they are not inconsistent with each other.

In another aspect, the invention further provides a pharmaceutical composition comprising lorlatinib free base (Form 7), according to any of the embodiments described herein, and a pharmaceutically acceptable carrier or excipient.

In another aspect, the invention provides a method of treating abnormal cell growth in a mammal, including a human, comprising administering to the mammal a therapeutically effective amount of lorlatinib free base (Form 7).

In another aspect, the invention provides a method of treating abnormal cell growth in a mammal, comprising administering to the mammal a therapeutically effective amount of a pharmaceutical composition comprising lorlatinib free base (Form 7), according to any of the aspects or embodiments described herein.

In another aspect, the invention provides use of lorlatinib free base (Form 7), or a pharmaceutical composition comprising such Form 7, according to any of the aspects or embodiments described herein, in a method of treating abnormal cell growth in a mammal.

In yet another aspect, the invention provides use of lorlatinib free base (Form 7), according to any of the aspects or embodiments described herein, in the manufacture of a medicament for the treatment of abnormal cell growth in a mammal.

In frequent embodiments, the abnormal cell growth is cancer. In one embodiment, the abnormal cell growth is cancer mediated by ALK or ROS1. In some such embodiments, the abnormal cell growth is cancer mediated by ALK.

In other such embodiments, the abnormal cell growth is cancer mediated by ROS1. In further embodiments, the abnormal cell growth is cancer mediated by at least one genetically altered tyrosine kinase, such as a genetically altered ALK or a genetically altered ROS1 kinase.

In some such embodiments, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma, and combinations thereof.

In other such embodiments, the cancer is selected from the group consisting of non-small cell lung cancer (NSCLC), squamous cell carcinoma, hormone-refractory prostate cancer, papillary renal cell carcinoma, colorectal adenocarcinoma, neuroblastoma, anaplastic large cell lymphoma (ALCL) and gastric cancer. In specific embodiments, the cancer is non-small cell lung cancer (NSCLC). In particular embodiments, the cancer is NSCLC mediated by ALK or ROS1, and more particularly, NSCLC mediated by a genetically altered ALK or a genetically altered ROS1.

DETAILED DESCRIPTION OF THE INVENTION

Figure 1:
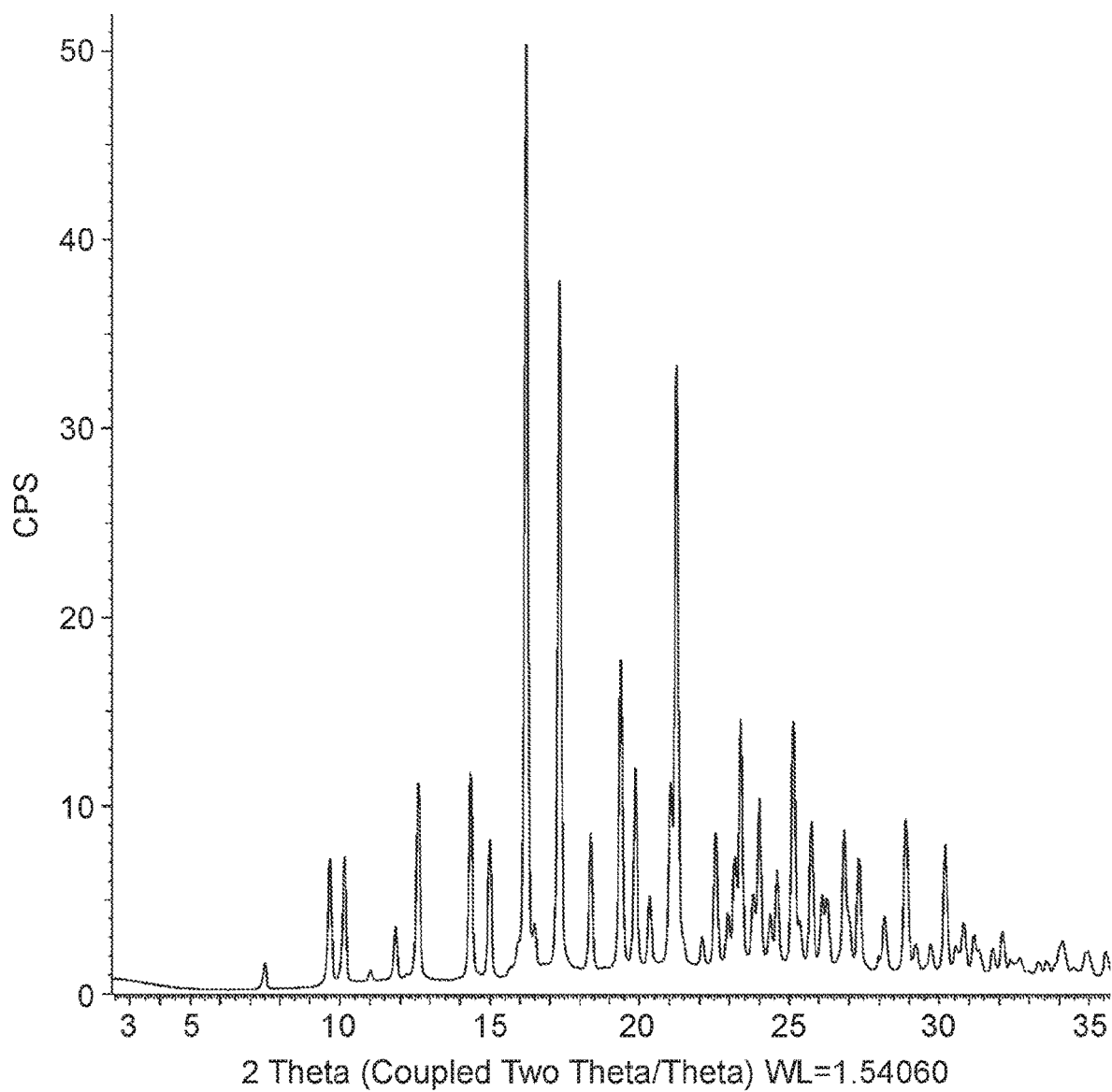
FIG. 1. PXRD pattern of lorlatinib free base (Form 7).

The present invention may be understood more readily by reference to the following detailed description of the embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The term "about" means having a value falling within an accepted standard of error of the mean, when considered by one of ordinary skill in the art.

As used herein, the term "essentially the same" means that variability typical for a particular method is taken into account. For example, with reference to X-ray diffraction peak positions, the term "essentially the same" means that typical variability in peak position and intensity are taken into account. One skilled in the art will appreciate that the peak positions (2θ) will show some variability, typically as much as ±0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, Raman spectrum wavenumber ($cm^{-1}$) values show variability, typically as much as ±2 $cm^{-1}$, while $^{13}C$ and $^{19}F$ solid state NMR spectrum (ppm) show variability, typically as much as ±0.2 ppm.

The term "crystalline" as used herein, means having a regularly repeating arrangement of molecules or external face planes. Crystalline forms may differ with respect to thermodynamic stability, physical parameters, x-ray structure and preparation processes.

The term "amorphous" refers to a disordered solid state.

The term "solvate" as used herein, means having on a surface, in a lattice or on a surface and in a lattice, a stoichiometric or non-stoichiometric amount of a solvent such as water, acetic acid, methanol, etc., or mixtures thereof, bound by non-covalent intermolecular forces. The term "hydrate" may be used specifically to describe a solvate comprising water.

The term "anhydrous" as used herein, means a crystalline form containing less than about 1% (w/w) of adsorbed moisture as determined by standard methods, such as a Karl Fisher analysis.

The invention described herein may be suitably practiced in the absence of any element(s) not specifically disclosed herein. Thus, for example, in each instance herein any of the terms "comprising", "consisting essentially of", and "consisting of" may be replaced with either of the other two terms.

In one aspect, the invention provides lorlatinib free base (Form 7). As disclosed herein, Form 7 is an anhydrous, non-solvated crystalline form of lorlatinib free base having physical stability, manufacturability and mechanical properties that are favorable for use in pharmaceutical formulations. The methods described herein provide lorlatinib free base (Form 7) which is substantially pure and free of alternative forms, including the solvated forms disclosed previously.

As described herein, Form 7 was characterized by PXRD, Raman spectroscopy, and $^{13}C$ and $^{19}F$ solid state NMR spectroscopy. Such crystalline forms may be further characterized by additional techniques, such as Fourier-Transform InfraRed Spectroscopy (FTIR), Differential Scanning Calorimetry (DSC), Thermogravimetric Analysis (TGA) or Differential Thermal Analysis (DTA).

In some embodiments of each of the aspects of the invention, lorlatinib free base (Form 7) is characterized by its powder X-ray diffraction (PXRD) pattern. In other embodiments of each of the aspects of the invention, lorlatinib free base (Form 7) is characterized by its Raman spectrum. In other embodiments of each of the aspects of the invention, lorlatinib free base (Form 7) is characterized by its $^{13}C$ solid state NMR spectrum. In still other embodiments of each of the aspects of the invention, lorlatinib free base (Form 7) is characterized by its $^{19}$F solid state NMR spectrum.

In further embodiments, lorlatinib free base (Form 7) is characterized by a combination of two, three or four of these methods. Exemplary combinations including two or more of the following are provided herein: powder X-ray diffraction (PXRD) pattern (2θ); Raman spectrum wavenumber values (cm$^{-1}$); $^{13}$C solid state NMR spectrum (ppm); or $^{19}$F solid state NMR spectrum (ppm). It will be understood that other combinations of two, three or four techniques may be used to uniquely characterize lorlatinib free base (Form 7) disclosed herein.

In one embodiment, lorlatinib free base (Form 7) has a PXRD pattern comprising one or more peaks at 2θ values selected from the group consisting of: 9.6, 10.1, 14.3, 16.2 and 17.3 °2θ±0.2 °2θ. In another embodiment, lorlatinib free base (Form 7) has a PXRD pattern comprising two or more peaks at 2θ values selected from the group consisting of: 9.6, 10.1, 14.3, 16.2 and 17.3 °2θ±0.2 °2θ. In another embodiment, lorlatinib free base (Form 7) has a PXRD pattern comprising three or more peaks at 2θ values selected from the group consisting of: 9.6, 10.1, 14.3, 16.2 and 17.3 °2θ±0.2 °2θ.

In another embodiment, Form 7 has a PXRD pattern comprising peaks at 2θ values of: 9.6, 10.1 and 16.2 °2θ±0.2 °2θ. In some such embodiments, Form 7 has a PXRD pattern further comprising a peak at the 2θ value of: 17.3 °2θ±0.2 °2θ. In other such embodiments, Form 7 has a PXRD pattern further comprising a peak at the 2θ value of: 14.3 °2θ±0.2 °2θ.

In another embodiment, lorlatinib free base (Form 7) has a PXRD pattern comprising a peak at a 2θ value of: 9.6 °2θ±0.2 °2θ. In another embodiment, Form 7 has a PXRD pattern comprising a peak at a 2θ value of: 10.1 °2θ±0.2 °2θ. In another embodiment, Form 7 has a PXRD pattern comprising a peak at a 2θ value of: 16.2 °2θ±0.2 °2θ. In another embodiment, Form 7 has a PXRD pattern comprising a peak at a 2θ values of: 17.3 °2θ±0.2 °2θ. In another embodiment, Form 7 has a PXRD pattern comprising peaks at 2θ values of: 9.6 and 10.1 °2θ±0.2 °2θ.

In another embodiment, lorlatinib free base (Form 7) has a PXRD pattern comprising peaks at 2θ values of: 9.6, 10.1, 16.2 and 17.3 °2θ±0.2 °2θ. In another embodiment, lorlatinib free base (Form 7) has a PXRD pattern comprising peaks at 2θ values of: 9.6, 10.1, 14.3 and 16.2 °2θ±0.2 °2θ. In yet another embodiment, lorlatinib free base (Form 7) has a PXRD pattern comprising peaks at 2θ values of: 9.6, 10.1, 14.3, 16.2 and 17.3 °2θ±0.2 °2θ. In some such embodiments, the PXRD pattern further comprises one or more additional peaks at 2θ values selected from the group consisting of the peaks in Table 1.

In specific embodiments, lorlatinib free base (Form 7) has a PXRD pattern comprising: (a) one, two, three, four, five, or more than five peaks selected from the group consisting of the peaks in Table 1 in °2θ±0.2 °2θ; (b) one, two, three, four, five, or more than five peaks selected from the group consisting of the characteristic peaks in Table 1 in °2θ±0.2 °2θ; or (c) peaks at 2θ values essentially the same as shown in FIG. 1.

In one embodiment, lorlatinib free base (Form 7) has a Raman spectrum comprising one or more wavenumber (cm$^{-1}$) values selected from the group consisting of: 774, 1553, 1619, 2229 and 2240 cm$^{-1}$±2 cm$^{-1}$. In another embodiment, lorlatinib free base (Form 7) has a Raman spectrum comprising two or more wavenumber (cm$^{-1}$) values selected from the group consisting of: 774, 1553, 1619, 2229 and 2240 cm$^{-1}$±2 cm$^{-1}$. In another embodiment, lorlatinib free base (Form 7) has a Raman spectrum comprising three or more wavenumber (cm$^{-1}$) values selected from the group consisting of: 774, 1553, 1619, 2229 and 2240 cm$^{-1}$±2 cm$^{-1}$.

In another embodiment, lorlatinib free base (Form 7) has a Raman spectrum comprising wavenumber (cm$^{-1}$) values of: 2229 and 2240 cm$^{-1}$±2 cm$^{-1}$. In another embodiment, lorlatinib free base (Form 7) has a Raman spectrum comprising a wavenumber (cm$^{-1}$) value of: 2229 cm$^{-1}$±2 cm$^{-1}$. In another embodiment, Form 7 has a Raman spectrum comprising a wavenumber (cm$^{-1}$) value of: 2240 cm$^{-1}$±2 cm$^{-1}$. In some such embodiments, Form 7 has a Raman spectrum further comprising the wavenumber (cm$^{-1}$) value of: 1619 cm$^{-1}$±2 cm$^{-1}$. In other such embodiments, Form 7 has a Raman spectrum further comprising the wavenumber (cm$^{-1}$) value of: 1553 cm$^{-1}$±2 cm$^{-1}$. In still other such embodiments, Form 7 has a Raman spectrum further comprising the wavenumber (cm$^{-1}$) value of: 774 cm$^{-1}$±2 cm$^{-1}$.

In another embodiment, Form 7 has a Raman spectrum comprising wavenumber (cm$^{-1}$) values of 1619, 2229 and 2240 cm$^{-1}$±2 cm$^{-1}$. In another embodiment, Form 7 has a Raman spectrum comprising wavenumber (cm$^{-1}$) values of: 1553, 2229 and 2240 cm$^{-1}$±2 cm$^{-1}$. In still another embodiment, Form 7 has a Raman spectrum comprising wavenumber (cm$^{-1}$) values of: 774, 2229 and 2240 cm$^{-1}$±2 cm$^{-1}$. In a further embodiment, Form 7 has a Raman spectrum comprising wavenumber (cm$^{-1}$) values of: 774, 1619, 2229 and 2240 cm$^{-1}$±2 cm$^{-1}$. In another embodiment, Form 7 has a Raman spectrum comprising wavenumber (cm$^{-1}$) values of: 774, 1553, 2229 and 2240 cm$^{-1}$±2 cm$^{-1}$. In yet another embodiment, Form 7 has a Raman spectrum comprising wavenumber (cm$^{-1}$) values of: 774, 1553, 1619, 2229 and 2240 cm$^{-1}$±2 cm$^{-1}$.

Figure 2:
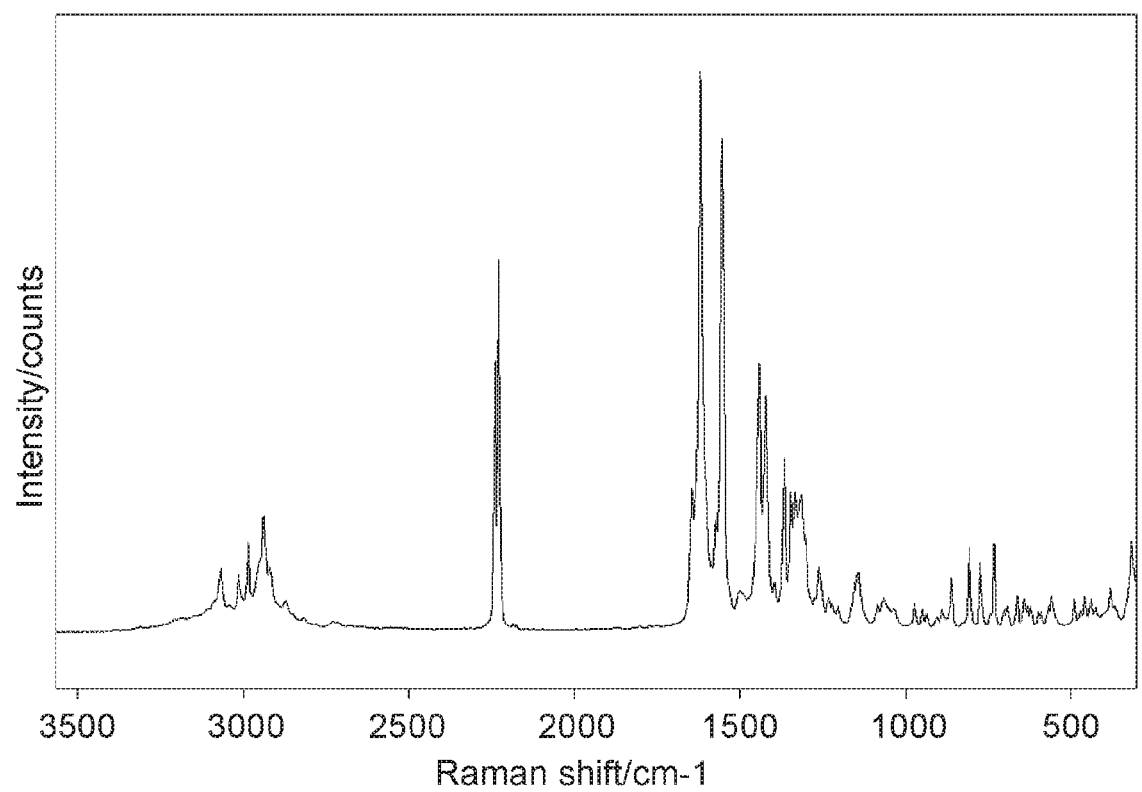
FIG. 2. FT-Raman spectrum of lorlatinib free base (Form 7).

In specific embodiments, lorlatinib free base (Form 7) has a Raman spectrum comprising: (a) one, two, three, four, five, or more than five wavenumber (cm$^{-1}$) values selected from the group consisting of the values in Table 2 in cm$^{-1}$±2 cm$^{-1}$; (b) one, two, three, four, five, or more than five wavenumber (cm$^{-1}$) values selected from the group consisting of the characteristic values in Table 2 in cm$^{-1}$±2 cm$^{-1}$; or (c) wavenumber (cm$^{-1}$) values essentially the same as shown in FIG. 2.

In one embodiment, lorlatinib free base (Form 7) has a $^{13}$C solid state NMR spectrum comprising one or more resonance (ppm) values selected from the group consisting of: 25.8, 39.1, 112.3, 117.7 and 142.1 ppm±0.2 ppm. In another embodiment, lorlatinib free base (Form 7) has a $^{13}$C solid state NMR spectrum comprising two or more resonance (ppm) values selected from the group consisting of: 25.8, 39.1, 112.3, 117.7 and 142.1 ppm±0.2 ppm. In another embodiment, lorlatinib free base (Form 7) has a $^{13}$C solid state NMR spectrum comprising three or more resonance (ppm) values selected from the group consisting of: 25.8, 39.1, 112.3, 117.7 and 142.1 ppm±0.2 ppm.

In some embodiments, lorlatinib free base (Form 7) has a $^{13}$C solid state NMR spectrum comprising the resonance (ppm) value of: 142.1 ppm±0.2 ppm. In another embodiment, Form 7 has a $^{13}$C solid state NMR spectrum comprising the resonance (ppm) value of: 39.1 ppm±0.2 ppm. In another embodiment, Form 7 has a $^{13}$C solid state NMR spectrum comprising the resonance (ppm) values of: 39.1 and 142.1 ppm±0.2 ppm. In some such embodiments, Form 7 has a $^{13}$C solid state NMR spectrum further comprising the resonance (ppm) value of: 112.3 ppm±0.2 ppm. In other such embodiments, Form 7 has a $^{13}$C solid state NMR spectrum further comprising the resonance (ppm) value of:

25.8 ppm±0.2 ppm. In still other such embodiments, Form 7 has a $^{13}$C solid state NMR spectrum further comprising the resonance (ppm) value of: 117.7 ppm±0.2 ppm.

In another embodiment, Form 7 has a $^{13}$C solid state NMR spectrum comprising the resonance (ppm) values of: 39.1, 112.3 and 142.1 ppm±0.2 ppm. In another embodiment, Form 7 has a $^{13}$C solid state NMR spectrum comprising the resonance (ppm) values of: 25.8, 39.1 and 142.1 ppm±0.2 ppm. In another embodiment, Form 7 has a $^{13}$C solid state NMR spectrum comprising the resonance (ppm) values of: 39.1, 117.7 and 142.1 ppm±0.2 ppm. In another embodiment, Form 7 has a $^{13}$C solid state NMR spectrum comprising the resonance (ppm) values of: 25.8, 39.1, 112.3, 117.7 and 142.1 ppm±0.2 ppm.

Figure 3:
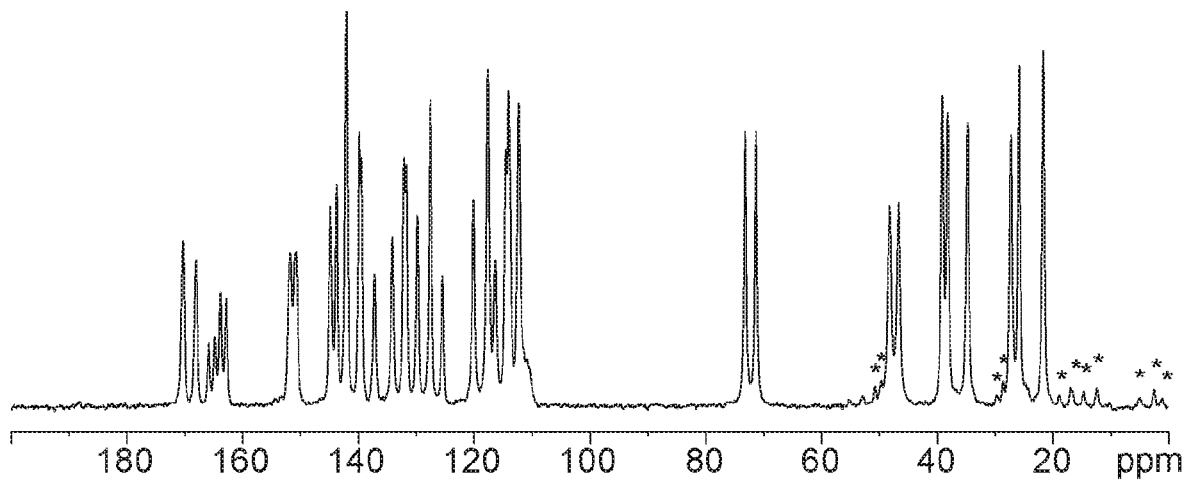
FIG. 3. Carbon CPMAS spectrum of lorlatinib free base (Form 7).

In specific embodiments, lorlatinib free base (Form 7) has a $^{13}$C solid state NMR spectrum (ppm) comprising: (a) one, two, three, four, five, or more than five resonance (ppm) values selected from the group consisting of the values in Table 3 in ppm±0.2 ppm; (b) one, two, three, four, five, or more than five resonance (ppm) values selected from the group consisting of the characteristic values in Table 3 in ppm±0.2 ppm; or (c) resonance (ppm) values essentially the same as shown in FIG. 3.

In one embodiment, lorlatinib free base (Form 7) has a $^{19}$F solid state NMR spectrum comprising one or more resonance (ppm) values selected from the group consisting of: −108.2 and −115.2 ppm±0.2 ppm.

In another embodiment, lorlatinib free base (Form 7) has a $^{19}$F solid state NMR spectrum comprising a resonance (ppm) value of: −115.2 ppm±0.2 ppm. In another embodiment, Form 7 has a $^{19}$F solid state NMR spectrum (ppm) comprising a resonance (ppm) value of: −108.2 ppm±0.2 ppm. In another embodiment, lorlatinib free base (Form 7) has a $^{19}$F solid state NMR spectrum comprising resonance (ppm) values of: −108.2 and −115.2 ppm±0.2 ppm.

Figure 4:
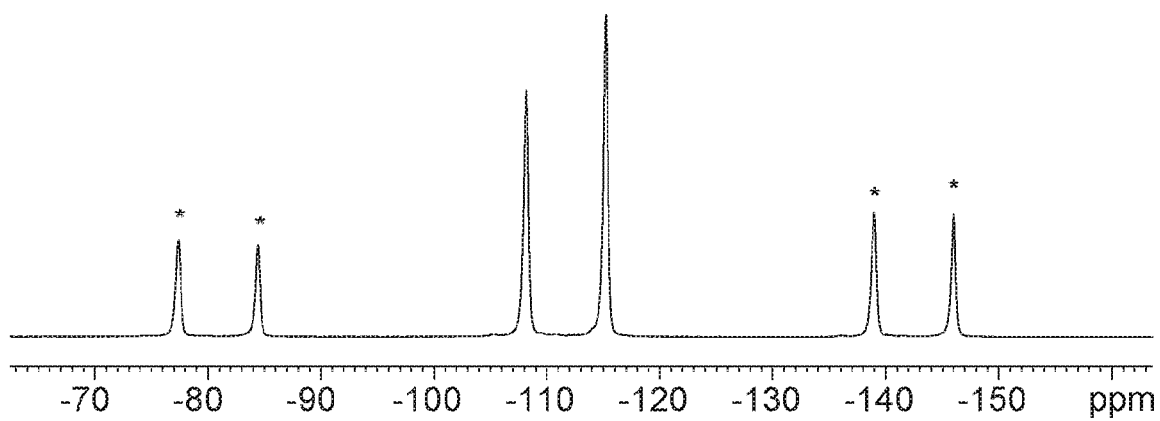
FIG. 4. Fluorine MAS spectrum of lorlatinib free base (Form 7).

In another embodiment, Form 7 has a $^{19}$F solid state NMR spectrum (ppm) comprising: (4) a $^{19}$F solid state NMR spectrum (ppm) comprising: (a) one or two resonance (ppm) values selected from the group consisting of the values in Table 4 in ppm±0.2 ppm; or (b) resonance (ppm) values essentially the same as shown in FIG. 4.

In further embodiments, lorlatinib free base (Form 7) is characterized by a combination of two, three or four of the embodiments described above that are not inconsistent with each other. Exemplary embodiments that may be used to uniquely characterize Form 7 of lorlatinib free base are provided below.

In one embodiment, lorlatinib free base (Form 7) has a powder X-ray diffraction pattern comprising peaks at 2θ values of: 9.6, 10.1 and 16.2 °2θ±0.2 °2θ.

In another embodiment, lorlatinib free base (Form 7) has a powder X-ray diffraction pattern comprising peaks at 2θ values of: 9.6, 10.1, 16.2 and 17.3 °2θ±0.2 °2θ.

In another embodiment, lorlatinib free base (Form 7) has a powder X-ray diffraction pattern comprising peaks at 2θ value of: 9.6, 10.1, 16.2 14.3 and 17.3 °2θ±0.2 °2θ.

In a further embodiment, lorlatinib free base (Form 7) has: (a) a powder X-ray diffraction pattern comprising peaks at 2θ value of: 9.6, 10.1, 16.2 °2θ±0.2 °2θ; and (b) a Raman spectrum comprising wavenumber (cm$^{-1}$) values of: 2229 and 2240 cm$^{-1}$±2 cm$^{-1}$.

In yet another embodiment, lorlatinib free base (Form 7) has: (a) a powder X-ray diffraction pattern comprising peaks at 2θ values of: 9.6, 10.1 and 16.2 °2θ±0.2 °2θ; and (b) a $^{13}$C solid state NMR spectrum comprising resonance (ppm) values of: 39.1 and 142.1 ppm±0.2 ppm.

In another embodiment, lorlatinib free base (Form 7) has a Raman spectrum comprising wavenumber (cm$^{-1}$) values of: 2229 and 2240 cm$^{-1}$±2 cm$^{-1}$.

In another embodiment, lorlatinib free base (Form 7) has a Raman spectrum comprising wavenumber (cm$^{-1}$) values of: 1619, 2229 and 2240 cm$^{-1}$±2 cm$^{-1}$.

In still another embodiment, lorlatinib free base (Form 7) has a Raman spectrum comprising wavenumber (cm$^{-1}$) values of: 1553, 1619, 2229 and 2240 cm$^{-1}$±2 cm$^{-1}$.

In yet another embodiment, lorlatinib free base (Form 7) has a Raman spectrum comprising wavenumber (cm$^{-1}$) values of: 774, 1553, 1619, 2229 and 2240 cm$^{-1}$±2 cm$^{-1}$.

In another embodiment, lorlatinib free base (Form 7) has: (a) a Raman spectrum comprising wavenumber (cm$^{-1}$) values of: 2229 and 2240 cm$^{-1}$±2 cm$^{-1}$; and (b) a $^{13}$C solid state NMR spectrum comprising resonance (ppm) values of: 39.1 and 142.1 ppm±0.2 ppm.

In another embodiment, lorlatinib free base (Form 7) has: (a) a Raman spectrum comprising wavenumber (cm$^{-1}$) values of: 2240 and 2229 cm$^{-1}$±2 cm$^{-1}$; and (b) a $^{19}$F solid state NMR spectrum comprising resonance (ppm) values of: −115.2 and −108.2 ppm±0.2 ppm.

In still another embodiment, lorlatinib free base (Form 7) has a $^{19}$F solid state NMR spectrum comprising the resonance (ppm) value of: −115.2 ppm±0.2 ppm.

In a further embodiment, lorlatinib free base (Form 7) has a $^{19}$F solid state NMR spectrum comprising resonance (ppm) values of: −115.2 and −108.2 ppm±0.2 ppm.

In another embodiment, lorlatinib free base (Form 7) has a $^{13}$C solid state NMR spectrum comprising resonance (ppm) values of: 39.1 and 142.1 ppm±0.2 ppm.

In another embodiment, lorlatinib free base (Form 7) has a $^{13}$C solid state NMR spectrum comprising resonance (ppm) values of: 39.1, 112.3 and 142.1 ppm±0.2 ppm.

In yet embodiment, lorlatinib free base (Form 7) has a $^{13}$C solid state NMR spectrum comprising resonance (ppm) values of: 25.8, 39.1, 112.3 and 142.1 ppm±0.2 ppm.

In still another embodiment, lorlatinib free base (Form 7) has a $^{13}$C solid state NMR spectrum comprising resonance (ppm) values of: 25.8, 39.1, 112.3, 117.7 and 142.1 ppm±0.2 ppm.

In another aspect, the invention provides a pharmaceutical composition comprising lorlatinib free base (Form 7) characterized according to any of the embodiments described herein, and a pharmaceutically acceptable carrier or excipient.

In another aspect, the invention provides method of treating abnormal cell growth in a mammal, preferably a human, comprising administering to the mammal a therapeutically effective amount of a pharmaceutical composition of the invention.

The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "mammal" refers to a human or animal subject. In certain preferred embodiments, the mammal is a human.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). In frequent embodiments of the methods provided herein, the abnormal cell growth is cancer.

As used herein "cancer" refers to any malignant and/or invasive growth or tumor caused by abnormal cell growth. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

In some embodiments, the abnormal cell growth is cancer mediated by an anaplastic lymphoma kinase (ALK). In some such embodiments, the ALK is a genetically altered ALK. In other embodiments, the abnormal cell growth is cancer mediated by ROS1 kinase. In some such embodiments, the ROS1 kinase is a genetically altered ROS1 kinase. In frequent embodiments, the abnormal cell growth is cancer, in particular NSCLC. In some such embodiments, the NSCLC is mediated by ALK or ROS1. In specific embodiments, the cancer is NSCLC is mediated by genetically altered ALK or genetically altered ROS1.

Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials include lactose or milk sugar and high molecular weight polyethylene glycols.

When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

EXAMPLES

The examples and preparations provided below further illustrate and exemplify particular aspects and embodiments of the invention. It is to be understood that the scope of the present invention is not limited by the scope of the following examples.

General Method 1. Powder X-Ray Diffraction (PXRD)

The PXRD data in FIG. 1 were collected according to the following general protocol.

Instrument Method:

PXRD patterns were collected on a Bruker-AXS Ltd. D4 powder X-ray diffractometer fitted with an automatic sample changer, a theta-theta goniometer, automatic beam divergence slit, and a PSD Vantec-1 detector. The X-ray tube voltage and amperage were set to 40 kV and 40 mA respectively. The diffractometer was aligned and a calibration check performed using a corundum reference material on the day of data collection. Data was collected at the Cu wavelength using a step size of 0.018 degrees and scan time of 11.3 hours scanning from 2.0 to 65.0 degrees 2-theta. The sample powders were prepared by placing the powder in a slightly greased low background holder. The sample powder was pressed by a glass slide to ensure that a proper sample height was achieved and rotated during collection. Data were collected using Bruker DIFFRAC software and analysis was performed by DIFFRAC EVA software (Version 3.1).

The PXRD patterns collected were imported into Bruker DIFFRAC EVA software. The measured PXRD pattern for Form 7 of the active pharmaceutical ingredient (API) was aligned with the simulated pattern from single crystal data prior to selecting the peak positions. A peak search was performed using the Bruker software. The peak selection was carefully checked to ensure that all peaks had been captured and all peak positions had been accurately assigned.

Peak Picking Method:

Peak picking was achieved using the peak search algorithm in the EVA software (Version 3.1). A threshold value of 1 and a width value of 0.27 (max 0.55, minimum 0.02) were used to make preliminary peak assignments. The output of automated assignments was visually checked to ensure validity and adjustments were manually made if necessary. Peak intensities were normalized relative to highest intensity peak equaling 100%. Peaks with relative intensity of 2% were generally chosen. A typical error of ±0.2° 2-theta in peak position applies to this data. The minor error associated with this measurement can occur as a result of a variety of factors including: (a) sample preparation (e.g., sample height), (b) instrument, (c) calibration, (d) operator (including those errors present when determining the peak locations), and (e) the nature of the material (e.g. preferred orientation and transparency errors). Therefore peaks are considered to have a typical associated error of ±0.2°

2-theta. When two peaks, in the list, are considered to overlap (±0.2° 2-theta) the less intense peak has been removed from the listing. Peaks existing as shoulders, on a higher intensity adjacent peak, have also been removed from the peak list.

Ideally the powder pattern should be aligned against a reference. This could either be the simulated powder pattern from the crystal structure of the same form, or an internal standard e.g. silica. The measured PXRD pattern for Form 7 of the API used to generate the peak listing in Table 1 was aligned to the simulated pattern from the single crystal structure.

General Method 2. Raman Spectroscopy

The Raman spectral data in FIG. 2 were collected according to the following general protocol.

Instrument Method:

Raman spectra were collected using a RAM II FT Raman module attached to a Vertex 70 FTIR spectrometer (Bruker, UK). The instrument is equipped with a 1064 nm Nd:YAG laser and a liquid nitrogen cooled germanium detector. Prior to data acquisition, instrument performance and calibration verifications were conducted using a white light source, and polystyrene and naphthalene references.

Samples were analyzed in truncated NMR tubes (5 mm diameter) that were spun during spectral collection. The backscattered Raman signal from the sample in the rotator was optimized and spectra from each sample were acquired using the following parameters:

Laser power: 500 mW
Spectral resolution: 2 cm$^{-1}$
Collection range: 4000-50 cm$^{-1}$
Number of scans: 512
Apodization function: Blackmann-Harris 4-term The variability in the peak positions in this experimental configuration is within ±2 cm$^{-1}$.

Peak Picking Method

Prior to peak picking the intensity scale of the Stokes scattered Raman signal was normalized to 1.00. Peaks positions were then identified using the peak picking functionality in the GRAMS/AI v.9.1 software (Thermo Fisher Scientific) with the threshold set to 0.007.

Peaks with relative intensities between 1.00 and 0.75, 0.74 and 0.30, and below 0.29 were labelled as strong, medium and weak respectively.

It is expected that, since FT-Raman and dispersive Raman are similar techniques, peak positions reported herein for FT-Raman spectra would be consistent with those which would be observed using a dispersive Raman measurement, assuming appropriate instrument calibration.

General Method 3. Solid state NMR (ssNMR) Spectroscopy:

The carbon CPMAS and fluorine MAS ssNMR data in FIGS. 3 and 4 were collected according to the following general protocol.

Instrument Method:

Solid state NMR (ssNMR) analysis was conducted at ambient temperature and pressure on a Bruker-BioSpin CPMAS probe positioned into a Bruker-BioSpin Avance III 500 MHz ($^1$H frequency) NMR spectrometer. The packed rotor was oriented at the magic angle and spun at 14.5 kHz. The carbon ssNMR spectrum was collected using a proton decoupled cross-polarization magic angle spinning experiment. A phase modulated proton decoupling field of 80-90 kHz was applied during spectral acquisition. The cross-polarization contact time was set to 2 ms and the recycle delay was set to 5 seconds. The number of scans was adjusted to obtain an adequate signal to noise ratio. The carbon spectrum was referenced using an external standard of crystalline adamantane, setting its upfield resonance to 29.5 ppm (as determined from neat TMS). The fluorine ssNMR spectrum was collected using a proton decoupled direct polarization magic angle spinning experiment. A phase modulated proton decoupling field of 80-90 kHz was applied during spectral acquisition. The recycle delay was set to 60 seconds. The number of scans was adjusted to obtain an adequate signal to noise ratio. The fluorine chemical shift scale was referenced using a direct polarization experiment on an external standard of 50/50 volume/volume of trifluoroacetic acid and water, setting its resonances to −76.54 ppm.

Peak Picking Method:

Automatic peak picking was performed using Bruker-BioSpin TopSpin version 3.2 software. Generally, a threshold value of 5% relative intensity was used to preliminary select peaks. The output of the automated peak picking was visually checked to ensure validity and adjustments were manually made if necessary.

Although specific $^{13}$C and $^{19}$F solid state NMR peak values are reported herein there does exist a range for these peak values due to differences in instruments, samples, and sample preparation. This is common practice in the art of solid state NMR because of the variation inherent in peak values. A typical variability for a $^{13}$C and $^{19}$F chemical shift x-axis value is on the order of plus or minus 0.2 ppm for a crystalline solid. The solid state NMR peak heights reported herein are relative intensities. The solid state NMR intensities can vary depending on the actual setup of the experimental parameters and the thermal history of the sample.

Example 1

Lab Scale Preparation of Form 7 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetra-decine-3-carbonitrile (lorlatinib) Free Base

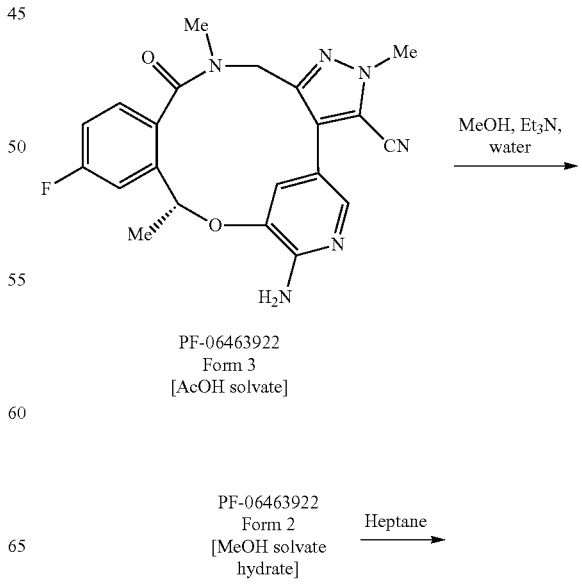

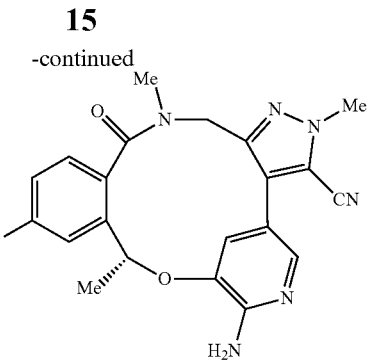

PF-06463922 Form 7

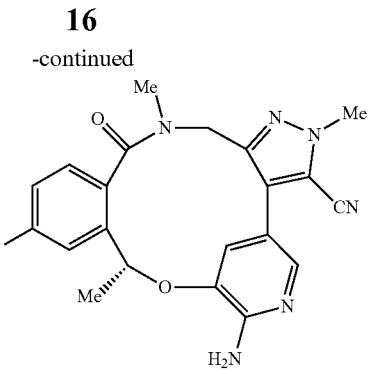

PF-06463922 Form 7

Form 7 of lorlatinib free base was prepared by de-solvation of the acetic acid solvate of lorlatinib (Form 3), prepared as described in International Patent Publication No. WO 2014/207606, via an intermediate methanol solvate hydrate form of lorlatinib (Form 2).

The acetic acid solvate of lorlatinib (Form 3) (5 g, 10.72 mmol) was slurried in methanol (10 mL/g, 1235.9 mmol) at room temperature in an Easymax flask with magnetic stirring to which triethylamine (1.2 equiv., 12.86 mmol) was added over 10 minutes. The resulting solution was heated to 60° C. and water (12.5 mL/g, 3469.3 mmol) was added over 10 minutes, while maintaining a temperature of 60° C. Crystallization was initiated by scratching the inside of the glass vessel to form a rapidly precipitating suspension which was triturated to make the system mobile. The suspension was then cooled to 25° C. over 1 hour, then cooled to 5° C. and granulated for 4 hours. The white slurry was filtered and washed with 1 mL/g chilled water/methanol (1:1) then dried under vacuum at 50° C. overnight to provide the methanol solvate hydrate Form 2 of lorlatinib.

Form 7 was then prepared via a re-slurry of the methanol solvate hydrate Form 2 of lorlatinib in heptane. 100 mg of lorlatinib Form 2 was weighed into a 4-dram vial and 3 mL of heptane was added. The mixture was slurried at room temperature on a roller mixer for 2 hours. Form conversion was confirmed by PXRD revealing complete form change to Form 7 of lorlatinib free base.

Example 2

Alternative Preparation of Form 7 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetra-decine-3-carbonitrile (lorlatinib) Free Base

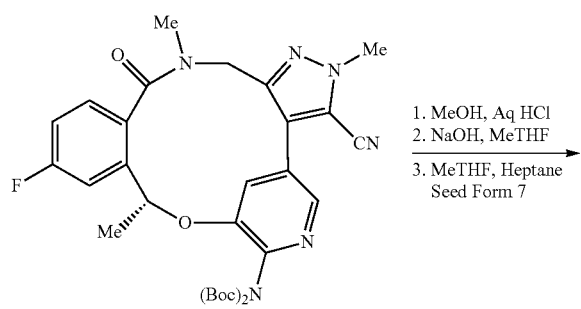

Into a 100 mL Easymax reactor equipped with an overhead stirrer, was added the bis-Boc protected macrocycle 1 (prepared as described in International Patent Publication No. WO 2014/207606 at Example 4) (7 g, 10 mmol) and methanol (28 mL; 4 mL/g of PF-06668559). The slurry was heated to 60° C. and treated with 6N hydrochloric acid (9 mL, 54 mmol) and held for 3 hours. Once reaction was determined complete, the mixture was cooled to 40° C. and treated with 1N sodium hydroxide (39 mL, 39 mmol) to partially neutralize the mixture. The mixture was treated with 2-methyltetrahydrofuran (53 mL), followed by neutralization to pH 7 with 1 N sodium hydroxide (13.5 mL, 13.5 mmol). The mixture was treated with sodium chloride (10.1 g, 173 mmol) and warmed to 60° C. The bottom aqueous layer was removed using a separatory funnel. The organic phase was washed with water (50 mL) at 60° C. The water wash was removed by separatory funnel. The organic layer was speck free filtered into a clean 125 mL reactor fitted with overhead agitator and distillation head. Additional 2-methyltetrahydrofuran (70 mL) was added to the organic mixture and the mixture was concentrated by atmospheric distillation to a volume of approximately 30 mL. The solution was treated with 2-methyltetrahydrofuran (12 mL) and adjusted to 60° C.

The solution was treated with n-heptane (10.5 mL), followed by seeding with Form 7 of lorlatinib free base (45 mg, 0.11 mmol). After aging the slurry for 1 hour, n heptane (73.5 mL) was added over 2 hours at 60° C. The resultant slurry was held for 1 hour at 60° C. followed by cooling to 20° C. over 1 hour and granulated for 16 hours. The slurry was filtered, and the product cake was washed with n heptane (12 mL). The solids were dried in the oven at 60° C. for 12 hours to give Form 7 of PF-0463922 free base (8.24 mmol, 3.36 g) as a white solid in 82% yield with >98% purity.

Characterization of Lorlatinib Free Base (Form 7)

PXRD Data

FIG. 1 shows PXRD data for lorlatinib free base (Form 7), collected according to General Method 1. A list of PXRD peaks at diffraction angles 2-Theta ° (°2θ)±0.2 °2θ and their relative intensities is provided in Table 1. Characteristic PXRD peaks distinguishing Form 7 are indicated by an asterisk (*).

TABLE 1

PXRD Peak List for Form 7 (2-Theta °)

| Angle °2θ ± 0.2 °2θ | Intensity % |
|---|---|
| 7.5 | 2.6 |
| 9.6* | 12.9 |
| 10.1* | 13.0 |
| 11.0 | 1.3 |
| 11.8 | 6.0 |
| 12.6* | 19.9 |
| 14.3* | 22.1 |
| 15.0 | 13.9 |
| 16.2* | 100.0 |
| 17.3* | 72.1 |
| 18.3 | 14.0 |
| 19.3* | 31.4 |
| 19.9 | 20.3 |
| 20.3 | 7.6 |
| 21.2 | 60.7 |
| 22.1 | 3.2 |
| 22.5 | 13.7 |
| 23.3 | 25.2 |
| 24.0 | 17.2 |
| 24.6 | 9.8 |

FT-Raman Data

FIG. 2 shows the FT-Raman spectrum of lorlatinib free base (Form 7), collected according to General Method 2. A list of FT-Raman peaks (cm$^{-1}$) and qualitative intensities is provided in Table 2 in cm$^{-1}$±2 cm$^{-1}$. Characteristic FT-Raman peaks (cm$^{-1}$) peaks distinguishing Form 7 are indicated by an asterisk (*). Normalized peak intensities are indicated as follows: W=weak; M=medium; S=strong.

TABLE 2

FT Raman Peak List for Form 7 (cm$^{-1}$)

| Wave number cm$^{-1}$ ± 2 cm$^{-1}$ | Normalized peak intensity |
|---|---|
| 3064 | w |
| 3012 | w |
| 2983 | w |
| 2937 | w |
| 2917 | w |
| 2871 | w |
| 2240* | m |
| 2229* | m |
| 1645 | w |
| 1619* | s |
| 1572 | w |
| 1553* | s |
| 1440 | m |
| 1422 | m |
| 1396 | w |
| 1367 | w |
| 1347 | w |
| 1335 | w |
| 1315 | m |
| 1301 | w |
| 1260 | w |
| 1232 | w |
| 1220 | w |
| 1203 | w |
| 1155 | w |
| 1143 | w |
| 1085 | w |
| 1068 | w |
| 1035 | w |
| 972 | w |
| 949 | w |
| 937 | w |
| 908 | w |
| 903 | w |
| 889 | w |
| 862 | w |
| 807 | w |
| 774* | w |
| 733 | w |
| 702 | w |
| 693 | w |
| 663 | w |
| 641 | w |
| 633 | w |
| 623 | w |
| 601 | w |
| 590 | w |
| 570 | w |
| 559 | w |
| 492 | w |
| 472 | w |
| 460 | w |
| 442 | w |
| 426 | w |
| 383 | w |
| 321 | w |
| 287 | w |
| 263 | w |
| 256 | w |
| 234 | w | ssNMR Data

FIG. 3 shows the carbon CPMAS spectrum of lorlatinib free base (Form 7), which was collected according to General Method 3. Chemical shifts are expressed in parts per million (ppm) and are referenced to external sample of solid phase adamantane at 29.5 ppm. A list of ssNMR $^{13}$C chemical shifts (ppm) for Form 7 is provided in Table 3 in ppm±0.2 ppm. Characteristic ssNMR $^{13}$C chemical shifts (ppm) distinguishing Form 7 are indicated by an asterisk (*).

TABLE 3 ssNMR $^{13}$C Chemical Shifts for Form 7 (ppm)

| $^{13}$C Chemical Shifts [ppm ± 0.2 ppm] | Intensity |
|---|---|
| 21.6 | 88 |
| 25.8* | 85 |
| 27.3 | 68 |
| 34.7 | 70 |
| 38.2 | 73 |
| 39.1* | 77 |
| 46.7 | 51 |
| 48.2 | 50 |
| 71.3 | 68 |
| 73.2 | 68 |
| 110.9 | 12 |
| 112.3* | 75 |
| 114.1 | 78 |
| 114.5 | 64 |
| 116.3 | 37 |
| 117.7* | 84 |
| 120.1 | 51 |
| 125.5 | 33 |
| 127.6 | 76 |
| 129.8 | 48 |
| 131.8 | 60 |
| 132.1 | 62 |
| 134.1 | 42 |
| 137.2 | 33 |
| 139.5 | 62 |
| 139.9 | 68 |
| 142.1* | 100 |
| 143.8 | 55 |
| 144.9 | 50 |

TABLE 3-continued ssNMR $^{13}$C Chemical Shifts for Form 7 (ppm)

| $^{13}$C Chemical Shifts [ppm ± 0.2 ppm] | Intensity |
|---|---|
| 150.8 | 39 |
| 151.8 | 38 |
| 162.8 | 27 |
| 163.8 | 29 |
| 164.9 | 17 |
| 165.9 | 16 |
| 168.1 | 37 |
| 170.3 | 41 |

FIG. 4 shows the fluorine MAS (ssNMR) spectrum of lorlatinib free base (Form 7), collected according to General Method 3. Chemical shifts are expressed in parts per million (ppm) referenced to an external sample of trifluoroacetic acid (50% V/V in H$_2$O) at −76.54 ppm.

The ssNMR $^{19}$F chemical shift (ppm) for Form 7 is provided in Table 4 in ppm±0.2 ppm. The characteristic ssNMR $^{19}$F chemical shifts (ppm) distinguishing Form 7 are indicated by an asterisk (*).

TABLE 4 ssNMR $^{19}$F Chemical Shifts for Form 7 (ppm)

| $^{19}$F Chemical Shifts [ppm ± 0.2 ppm] | Intensity |
|---|---|
| −115.2* | 100 |
| −108.2* | 76 |

Example 3

Representative Drug Product Formulations of Lorlatinib Free Base (Form 7)

Immediate release (IR) tablets comprising lorlatinib free base (Form 7) may be prepared using conventional excipients commonly used in tableted formulations.

Tablets typically contain from 1-30% of lorlatinib on a w/w basis. Microcrystalline cellulose, dibasic calcium phosphate anhydrous (DCP) and lactose monohydrate may be used as tablet fillers, and sodium starch glycolate may be used as a disintegrant. Magnesium stearate may be used as a lubricant.

A typical IR tablet formulation of Form 7 containing Dibasic Calcium Phosphate Anhydrous (DCP) as a tablet filler (DCP tablet) is provided in Table 5.

TABLE 5

Typical Composition of IR Tablet using Dibasic Calcium Phosphate Anhydrous (DCP) as a tablet filler

| | | % composition |
|---|---|---|
| Form 7 | Active Ingredient | 1-30 |
| Microcrystalline Cellulose | Filler | 35-60 |
| Dibasic Calcium Phosphate Anhydrous | Filler | 10-35 |
| Sodium Starch Glycolate | Disintegrant | 2-5 |
| Magnesium Stearate | Lubricant | 0.5-1.5 |
| Total Tablet Weight | | 100.0 |

A typical IR tablet formulation of Form 7 containing lactose as a tablet filler (lactose tablet) is provided in Table 6.

TABLE 6

Typical Composition of IR Tablet using lactose as a tablet filler

| | | % composition |
|---|---|---|
| Form 7 | Active Ingredient | 1-30 |
| Microcrystalline Cellulose | Filler | 35-60 |
| Lactose monohydrate | Filler | 10-35 |
| Sodium Starch Glycolate | Disintegrant | 2-5 |
| Magnesium Stearate | Lubricant | 0.5-1.5 |
| Total Tablet Weight | | 100.0 |

IR tablets of lorlatinib free base (Form 7) may be manufactured using a dry granulation process prior to compression. In this process the crystalline material is blended with some proportion of the excipients falling within the ranges outline above and the blend is dry granulated using a roller compactor. The granule is milled as part of this process. The granules are blended with remainder of any of the excipients (e.g., magnesium stearate) prior to compression.

Figure 5:
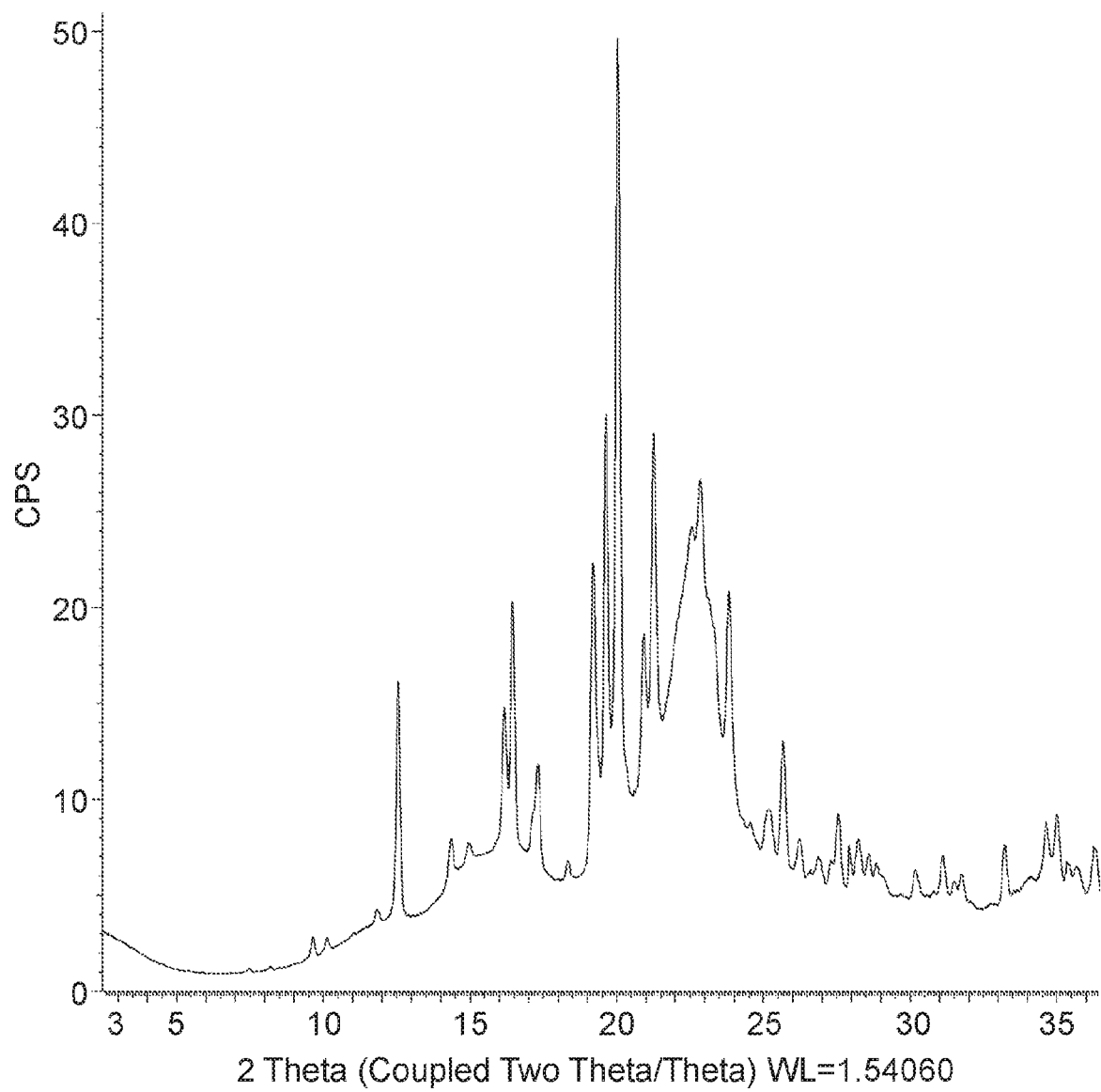
FIG. 5. PXRD pattern of lactose tablet of lorlatinib free base (Form 7).
Figure 6:
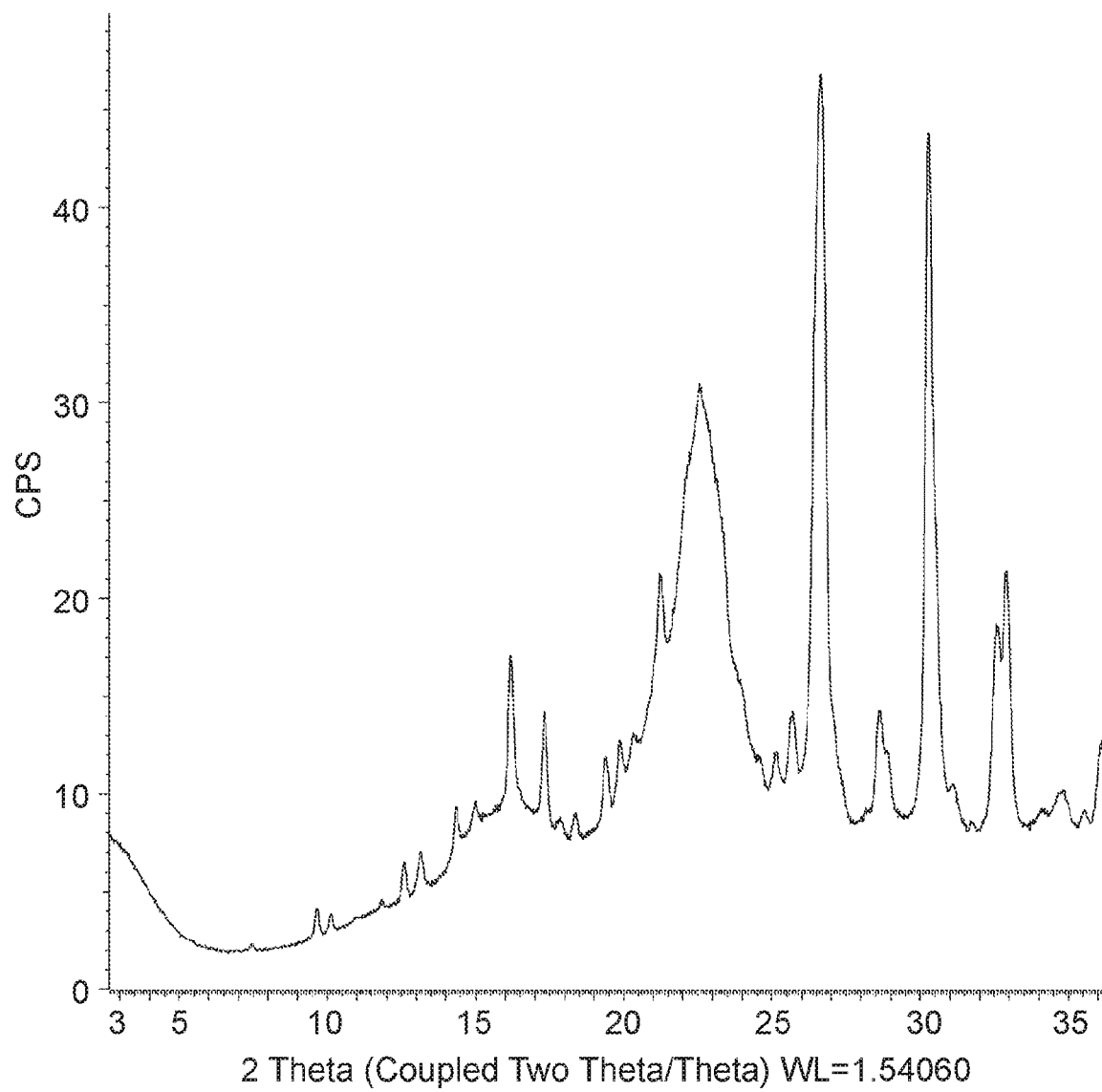
FIG. 6. PXRD pattern of dibasic calcium phosphate (DCP) tablet of lorlatinib free base (Form 7).
Figure 7:
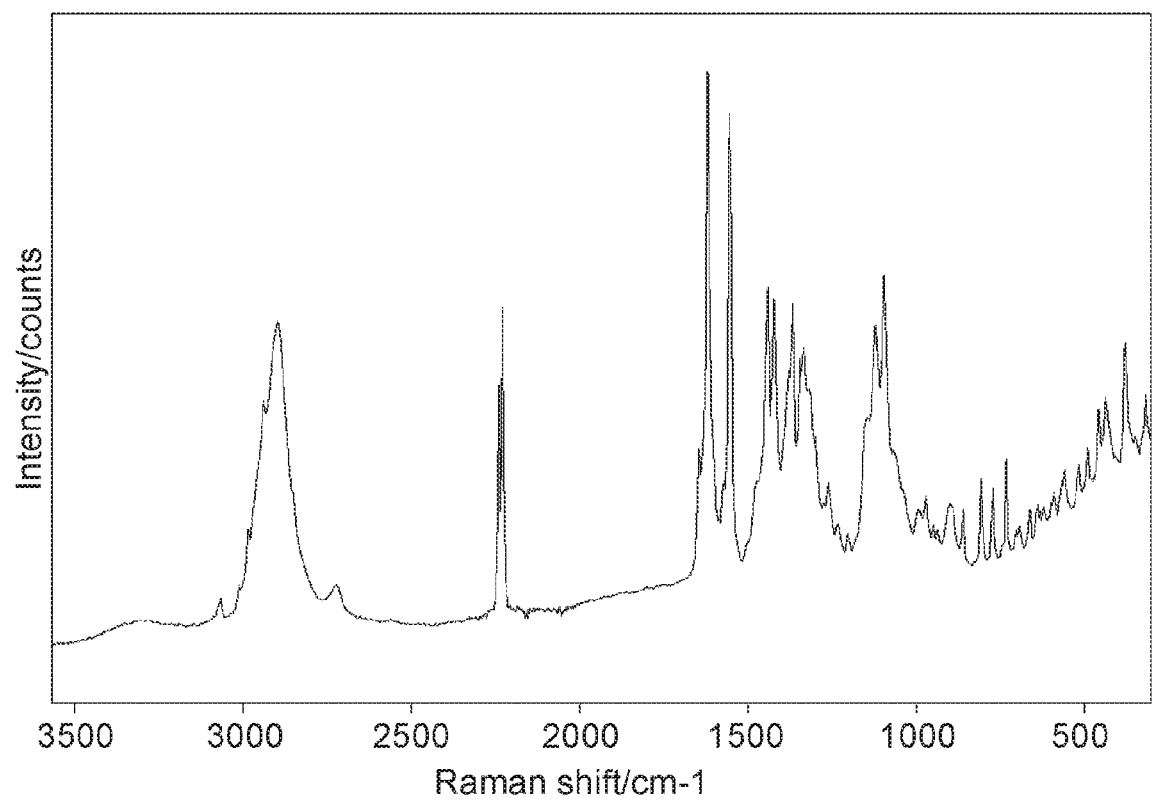
FIG. 7. FT-Raman spectrum of lactose tablet of lorlatinib free base (Form 7).
Figure 8:
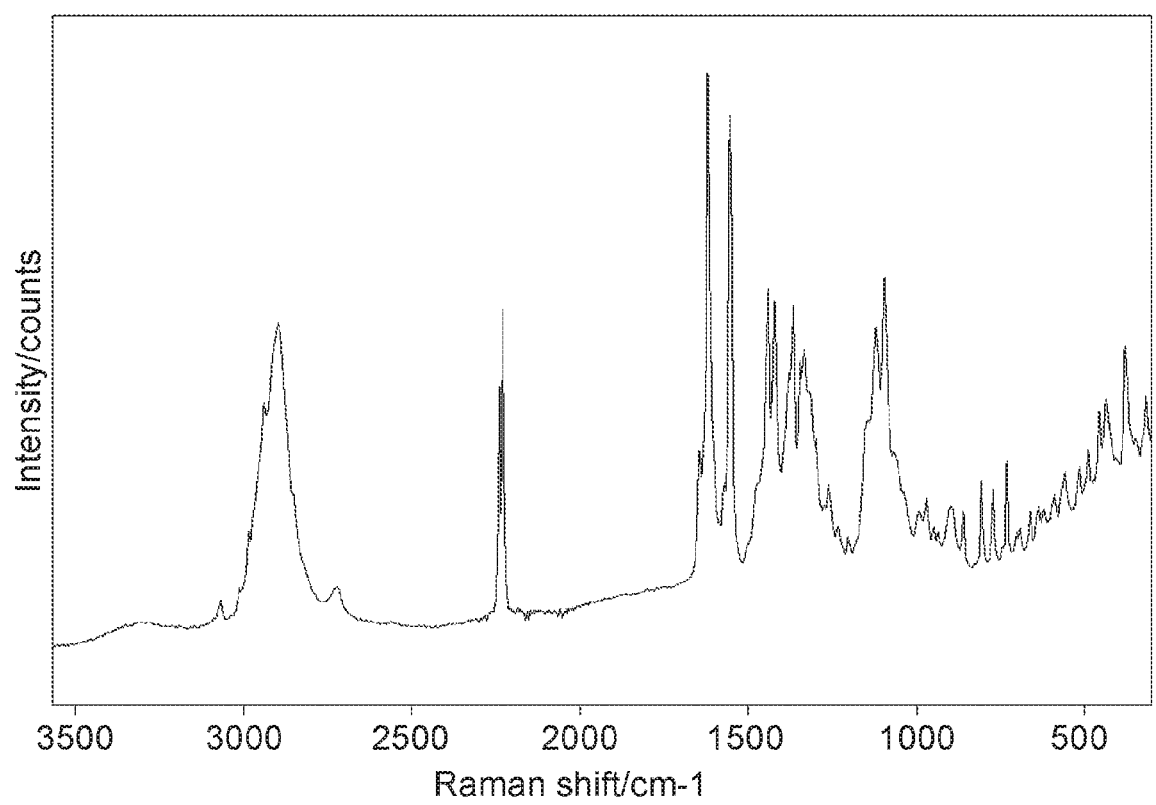
FIG. 8. FT-Raman spectrum of DCP tablet of lorlatinib free base (Form 7).

FIGS. 5 and 6 show the PXRD patterns of a prototype lactose tablet and DCP tablet, respectively, comprising 10% w/w of lorlatinib free base (Form 7). FIGS. 7 and 8 show the FT-Raman spectrum of a prototype lactose tablet and DCP tablet, respectively, comprising 10% w/w of lorlatinib free base (Form 7).

Example 4

Thermodynamic Stability of Lorlatinib Free Base (Form 7)

The thermodynamic stability of anhydrous lorlatinib free base (Form 7) was evaluated employing slurry experiments under a range of water activity and temperature conditions. Suspensions of Form 7 were equilibrated for two weeks in diverse solvent systems at three different temperatures: 5° C., room temperature and 40° C. and water activities 0.25 to 1.00. After 2 weeks, the solids in equilibrium were isolated and the solid form was evaluated by PXRD.

The results summarized in Table 7 demonstrate that anhydrous Form 7 API could form solvated forms in several solvent systems and a hydrate in pure water, but does not convert to a different anhydrous solid state under the conditions explored.

TABLE 7

Slurry Output for anhydrous lorlatinib Form 7. Form 5, 13, 16 and 20 are solvated forms of the lorlatinib free base and Form 18 is a hydrate.

| Solvent | Water activity | 5° C. | RT | 40° C. |
|---|---|---|---|---|
| nBuOH | 0 | Form 7 | Form 20 | Form 7 |
| iProAc | 0 | Form 7 | Form 7 | Form 7 |
| MiBK | 0 | Form 7 | Form 7 | Form 7 |
| TBME | 0 | Form 7 | Form 7 | Form 7 |
| Toluene | 0 | Form 7 | Form 7 | Form 7 |
| IPA | 0.25 | Form 16 | Form 7 | Form 7 |
| IPA | 0.50 | Form 13 | Form 13 | Form 5 |
| IPA | 0.70 | Form 13 | Form 13 | Form 5 |
| IPA | 0.90 | Form 13 | Form 13 | Form 13 |
| Water | 1.00 | Form 7 + Form 18 | Form 18 | Form 7 |

Example 5

Solid-State Physical Stability of Anhydrous Lorlatinib Free Base (Form 7) and Drug Product The physical stability of anhydrous lorlatinib free base (Form 7) API was investigated at elevated relative humidities (% RH) for extended time period and at accelerated stability conditions for shorter period. Form 7 stored at ambient temperature and humidity levels of 75% RH and 90% RH for 12 months and at 70° C./75% RH and 80° C./75% RH for 1 week did not undergo any physical change. Results are shown in Table 8.

TABLE 8

Long term stability of Form 7 API

| Conditions | Time | Solid Form |
|---|---|---|
| 75% RH, ambient temperature | 12 months | Form 7 |
| 90% RH, ambient temperature | 12 months | Form 7 |
| 70° C./75% RH | 1 week | Form 7 |
| 80° C./40% RH | 1 week | Form 7 |

A representative drug product formulation of Form 7 demonstrated superior physical stability relative to the acetic acid solvate of lorlatinib free base disclosed in WO 2014/207606.

The physical stabilities of lorlatinib Form 7 and acetic acid solvate in the drug product were investigated under a variety of conditions using FT-Raman and Solid State NMR spectroscopy. Results are summarized in Table 9.

TABLE 9

Physical stability of Form 7 drug product vs. acetic acid solvate comparing amount of physical impurity

| Conditions | Time | lorlatinib acetic acid solvate | lorlatinib free base Form 7 |
|---|---|---|---|
| 70° C./75% RH | 1 week | impurity >50% | No change detected |
| 50° C./75% RH | 2 weeks | >10% impurity <50% | No change detected |
| 70° C./40% RH | 2 weeks | impurity >50% | No change detected |
| 70° C./10% RH | 3 weeks | impurity >50% | No change detected |
| 25° C./60% RH | 12 months | >10% impurity <50% | No change detected |
| 30° C./65% RH | 12 months | >10% impurity <50% | No change detected |

TABLE 10

Summary of physical stability studies for Lorlatinib Free Base Form 7 for several drug product formulations

| Conditions | Excipients | Time | Output Solid Form |
|---|---|---|---|
| 50° C./75% RH | tablet with lactose, magnesium stearate, Polyplasdone XL | 2 weeks | Form 7 |
| 50° C./75% RH | tablet with DCP, stearic acid, Explotab | 2 weeks | Form 7 |
| 50° C./75% RH | tablet with mannitol, magnesium stearate, Explotab | 2 weeks | Form 7 |
| 50° C./75% RH | tablet with DCP, stearic acid, Polyplasdone XL | 2 weeks | Form 7 |
| 50° C./75% RH | tablet with lactose, stearic acid, Explotab | 2 weeks | Form 7 |
| 50° C./75% RH | tablet with DCP, magnesium stearate, Polyplasdone XL | 2 weeks | Form 7 |
| 50° C./75% RH | tablet with mannitol, stearic acid, Polyplasdone XL | 2 weeks | Form 7 |
| 50° C./75% RH | tablet with DCP, magnesium stearate, Explotab | 2 weeks | Form 7 |

Example 6

Representative Tablet Formulations

Immediate release, film coated tablets were prepared in 25 mg, 50 mg and 100 mg immediate dosages using a dry granulation manufacturing process. The compositions of the tablets are provided in Table 11.

TABLE 11

Compositions of IR tablets of three different strengths

| Component | Component Role | 25 mg tablet (mg/tablet) | 50 mg tablet (mg/tablet) | 100 mg tablet (mg/tablet) |
|---|---|---|---|---|
| lorlatinib free base (Form 7) | Active ingredient | 25.000 | 50.000 | 100.00 |
| Microcrystalline Cellulose | Filler | 143.325 | 286.650 | 355.540 |
| Dibasic Calcium Phosphate Anhydrous | Filler | 71.675 | 143.350 | 177.800 |
| Sodium Starch Glycolate | Disintegrant | 7.500 | 15.000 | 20.000 |
| Magnesium Stearate | Lubricant | 2.500 | 5.000 | 13.330 |
| Tablet core weight | | 250.00 | 500.00 | 666.670 |
| Opadry II Tan or Lavender | Coating agent | 7.500 | 15.000 | 20.000 |
| Sterile water for irrigation* | | (42.500) | (85.000) | (113.330) |
| Total weight (mg) | | 257.500 | 515.000 | 686.670 |

*removed during processing. Does not appear in final product

Example 7

Chemical Stability of Representative Tablet Formulation

Chemical stability data was generated at 25° C./60% RH and 30° C./75% RH for 12 months and at 40° C./75% RH for 6 months for the 25 mg tablets prepared according to Example 6. Three main degradation products (amide, formaldehyde dimer and oxidative photodegradant) were monitored to assess the chemical stability of the test formulation. The chemical stability data for these chemical impurities is provided in Table 12.

TABLE 12

Summary of chemical stability data for 25 mg
IR film coated tablet of lorlatinib Form 7

| Impurity | 12 months 25° C./60% RH | 12 months 30° C./75% RH | 6 months 40° C./75% RH |
| --- | --- | --- | --- |
| amide | NMT 0.05 | 0.08 | 0.15 |
| dimer | 0.09 | 0.16 | 0.19 |
| photodegradant | NMT 0.05 | NMT 0.05 | NMT 0.05 |

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

We claim:

1. A solid dosage form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (lorlatinib) free base (Form 7), wherein the dosage form has a powder X-ray diffraction (PXRD) pattern comprising peaks at 2θ values of: 9.6, 10.1 and 16.2 °2θ±0.2 °2θ.

2. The dosage form of claim 1, wherein the dosage form is a tablet, wherein the tablet comprises a tablet core.

3. The tablet of claim 2, wherein the tablet core is 1-30% of lorlatinib free base (Form 7) on a w/w basis.

4. The tablet of claim 3, wherein the tablet core is about 10% of lorlatinib free base (Form 7) on a w/w basis.

5. The tablet of claim 3, wherein the tablet core is about 15% of lorlatinib free base (Form 7) on a w/w basis.

6. The tablet of claim 2, wherein the tablet core further comprises a filler.

7. The tablet of claim 6, wherein the filler is microcrystalline cellulose, dibasic calcium phosphate anhydrous, lactose monohydrate, or a combination thereof.

8. The tablet of claim 7, wherein the filler is microcrystalline cellulose.

9. The tablet of claim 8, wherein the tablet core is 35-60% microcrystalline cellulose on a w/w basis.

10. The tablet of claim 9, wherein the tablet core is about 53% microcrystalline cellulose on a w/w basis.

11. The tablet of claim 9, wherein the tablet core is about 58% microcrystalline cellulose on a w/w basis.

12. The tablet of claim 7, wherein the filler is dibasic calcium phosphate anhydrous.

13. The tablet of claim 12, wherein the tablet core is 10-35% dibasic calcium phosphate anhydrous on a w/w basis.

14. The tablet of claim 13, wherein the tablet core is about 29% dibasic calcium phosphate anhydrous on a w/w basis.

15. The tablet of claim 13, wherein the tablet core is about 27% dibasic calcium phosphate anhydrous on a w/w basis.

16. The tablet of claim 7, wherein the filler is lactose monohydrate.

17. The tablet of claim 16, wherein the tablet core is 35% lactose monohydrate on a w/w basis.

18. The tablet of claim 2, wherein the tablet core further comprises a disintegrant.

19. The tablet of claim 18, wherein the disintegrant is starch, alginic acid, silicates, or a combination thereof.

20. The tablet of claim 19, wherein the starch is sodium starch glycolate.

21. The tablet of claim 20, wherein the tablet core is 2-5% sodium starch glycolate on a w/w basis.

22. The tablet of claim 21, wherein the tablet core is about 3% sodium starch glycolate on a w/w basis.

23. The tablet of claim 2, wherein the tablet core further comprises a lubricant.

24. The tablet of claim 23, wherein the lubricant is magnesium stearate, sodium lauryl sulfate, talc, or a combination thereof.

25. The tablet of claim 24, wherein the lubricant is magnesium stearate.

26. The tablet of claim 25, wherein the tablet core is 0.5-2.5% magnesium stearate on a w/w basis.

27. The tablet of claim 26, wherein the tablet core is about 1% magnesium stearate on a w/w basis.

28. The tablet of claim 26, wherein the tablet core is about 2% magnesium stearate on a w/w basis.

29. The tablet of claim 2, wherein the tablet further comprises a film coating having a film coating weight.

30. The tablet of claim 29, wherein the film coating is Opadry II Tan or Opadry II Lavender.

31. The tablet of claim 29, wherein the film coating weight is about 3% on a w/w basis of the tablet core weight.

32. The tablet of claim 2, wherein the tablet comprises about 25 mg or about 50 mg or about 100 mg (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (lorlatinib) free base (Form 7).

33. The tablet of claim 2, wherein the tablet consists of: 25 mg (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (lorlatinib) free base; 143.325 mg microcrystalline cellulose; 71.675 mg dibasic calcium phosphate anhydrous; 7.500 mg sodium starch glycolate; 2.500 mg magnesium stearate; and 7.500 mg Opadry II Tan.

34. The tablet of claim 2, wherein the tablet consists of: 50 mg (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (lorlatinib) free base; 286.650 mg microcrystalline cellulose; 143.350 mg dibasic calcium phosphate anhydrous; 15.000 mg sodium starch glycolate; 5.000 mg magnesium stearate; and 15.000 mg Opadry II Lavender.

35. The tablet of claim 2, wherein the tablet consists of: 100 mg (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (lorlatinib) free base; 355.540 mg microcrystalline cellulose; 177.800 mg dibasic calcium phosphate anhydrous; 20.000 mg sodium starch glycolate; 13.330 mg magnesium stearate; and 20.000 mg Opadry II Lavender.

36. A tablet comprising 1-30% of lorlatinib free base (Form 7), 35-60% microcrystalline cellulose; 10-35% dibasic calcium phosphate anhydrous; 2-5% sodium starch glycolate; and 0.5-2.5% magnesium stearate; on a w/w basis, wherein the tablet has a powder X-ray diffraction (PXRD) pattern comprising peaks at 2θ values of: 9.6, 10.1 and 16.2 °2θ±0.2 °2θ.

37. A tablet comprising 1-30% of lorlatinib free base (Form 7), 35-60% microcrystalline cellulose; 10-35% lactose monohydrate; 2-5% sodium starch glycolate; and 0.5-1.5% magnesium stearate; on a w/w basis, wherein the tablet has a powder X-ray diffraction (PXRD) pattern comprising peaks at 2θ values of: 9.6, 10.1 and 16.2 °2θ±0.2 °2θ.

\* \* \* \* \*